United States Patent [19]

Manschot et al.

[11] E Re. 30,607

[45] Reissued May 12, 1981

[54] COMBINATION URINE METER AND DRAINAGE RECEPTACLE

[75] Inventors: James G. Manschot, Eagle; Byron L. Mather; Larry A. Salvadori, both of Milwaukee, all of Wis.

[73] Assignee: Plastronics, Inc., Milwaukee, Wis.

[21] Appl. No.: 49,060

[22] Filed: Jun. 18, 1979

Related U.S. Patent Documents

Reissue of:

[64] Patent No.: 4,095,589
Issued: Jun. 20, 1978
Appl. No.: 573,853
Filed: May 20, 1975

[51] Int. Cl.[3] ..... A61B 19/00

[52] U.S. Cl. ..... 128/762; 128/767; 128/768; 128/771; 128/295

[58] Field of Search ..... 128/761, 762, 767, 768, 128/771, 275, 295; 4/113.1, 144.2; 73/427

[56] References Cited

U.S. PATENT DOCUMENTS

| | | | |
|---|---|---|---|
| Re. 26,964 | 10/1970 | Coanda | 128/762 |
| 3,298,370 | 1/1967 | Beatty | 128/295 |
| 3,601,119 | 8/1971 | Engelsher | 128/762 |
| 3,683,894 | 8/1972 | Villari | 128/767 |
| 3,774,591 | 11/1973 | Corbin et al. | 128/761 |
| 3,776,231 | 12/1973 | Holbrook et al. | 128/275 |
| 3,830,107 | 8/1974 | Linzer et al. | 128/761 |
| 3,831,453 | 8/1974 | McWhorter | 128/771 |
| 3,888,126 | 6/1975 | Cross | 128/771 |
| 3,888,236 | 6/1975 | Marx | 128/767 |

*Primary Examiner*—Kyle L. Howell
*Attorney, Agent, or Firm*—Michael, Best & Friedrich

[57] ABSTRACT

A combination urine meter and drainage receptacle including a liquid meter of semi-rigid transparent material and a flexible liquid drainage receptacle. The meter and drainage receptacle are connected together at the upper portions thereof by a semi-rigid tubular assembly having a flow conduit therethrough of relatively large diameter and short longitudinal length. Drainage of liquid from the meter to the receptacle can be simply and effectively accomplished by tilting the meter with respect to the flexible receptacle from a vertical hanging position to a drainage position. When so tilted, the drainage bag will retain its substantially vertical hanging position to insure a positive drainage flow between the two containers.

14 Claims, 4 Drawing Figures

COMBINATION URINE METER AND DRAINAGE RECEPTACLE

Matter enclosed in heavy brackets [ ] appears in the original patent but forms no part of this reissue specification; matter printed in italics indicates the additions made by reissue.

BACKGROUND OF THE INVENTION

I. Field of the Invention

This invention relates to a combination urine meter and drainage receptacle.

II. Description of the Prior Art

The most pertinent prior art known to applicants is shown and described in U.S. Pat. Nos. 3,683,984, 3,601,119 and 3,345,980. The principal advantages of the present invention over such prior art is its simplicity of design and the ease and effectiveness of the means of draining the urine from the meter into the drainage receptacle.

SUMMARY OF THE INVENTION

A combination urine meter and drainage receptacle comprising a liquid meter having at least one volume calibrated chamber and an inlet opening through which liquid may be introduced into such chamber. A liquid drainage receptacle of flexible material is connected to the meter and is in fluid communication therewith by means of a fluid communication means connected between the upper portions of the meter and drainage receptacle. The liquid communication means is adapted to permit relative movement of the meter with respect to the drainage receptacle to thereby facilitate drainage of liquid from the interior of the meter through the fluid conduit and into the drainage receptacle by simply tilting the meter with respect to the receptacle, such tilting movement of the meter being accomplished without disturbing the relative vertical hanging position of the receptacle.

DESCRIPTION OF THE PREFERRED EMBODIMENT

Figure 1:
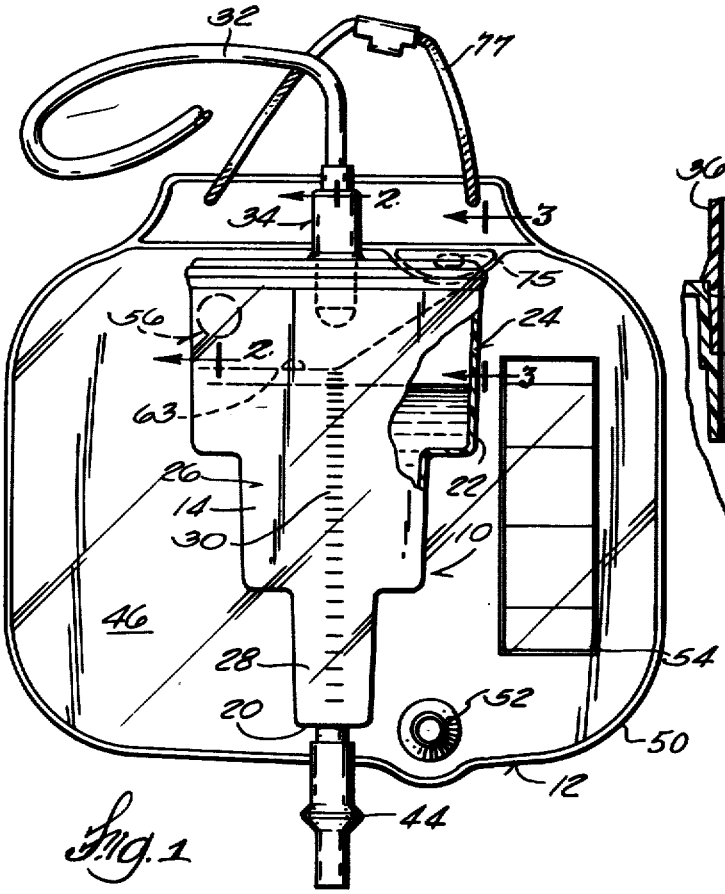
FIG. 1 is a front elevation view (with parts broken away) of a preferred embodiment of the combination urine meter and drainage receptacle of this invention.

The combination of the present invention is comprised of two basic parts, namely a urine meter 10 and a drainage receptacle 12.

The urine meter 10 is comprised of a front wall 14, a rear wall 16, a top wall 18, a bottom wall 20 and side walls 22,22 defining a semi-rigid container with an upper section 24, an intermediate section 26 of smaller internal volume per unit of height than the upper section and a lower section 28 of smaller internal volume per unit of height than the intermediate section.

As shown in FIG. 1, a scale 30 is molded in or printed on the surface of the front wall 14 of the urine meter 10.

The scale 30 serves as an indication of the volume of liquid in the meter. Since the lowermost section 28 of the meter is of smaller volume than the intermediate section 26, the scale markings for a given unit of volume measurement will be spaced further apart on such lower section than on the intermediate section to thereby facilitate the accurate measurement of smaller volumes of liquid in the lower section. The same is true with respect to the relationship of intermediate section 26 and the upper section 24. In the preferred embodiment the meter is made of transparent material such as clear cellulose propionate plastic. The use of a transparent material permits a volume reading to be made on the scale 30 and also permits the determination of urine coloration changes which may occur.

A hollow tube 32 opens into the interior of the meter 10 through a drip tube assembly 34 mounted in the top wall 18 of the meter. The tube 32 serves as a conduit through which fluid such as urine may pass into the meter from a body, such fluid originally being removed from the body through a catheter or similar device (not shown).

Drip tube assembly 34 is comprised of an upper tubular member 36 and a lower tubular drip projection 38 formed integrally with the top wall 18 of the meter. Member 36 is telescopically engaged with the projection 38 and is sealed therein by a suitable adhesive. A shoulder 40 is provided on member 36 to facilitate its installation in projection 38. Projection portion 38 has an opening 42 in the bottom portion thereof through which liquid flowing through tube 32 enters the interior of the meter. Said drip projection 38 is in the form of a sealed tube having a rounded end with said end having a cut-out portion to provide the opening 42.

Mounted in the bottom wall 20 of urine meter 10 is a sampling valve 44 which may be opened and closed to drain fluid from the interior of the meter. Any one of a number of commercially available valves such as push-pull valves or faucet type valves may be suitable for use as a drainage valve 44. Valve 44 shown in the drawings is a push-pull type valve which is opened by pulling down on its lower portion and closed by a reverse movement thereof.

Drainage receptacle 12 is comprised of a front sheet 46 and a back sheet 48 of fluid impervious flexible material. The front sheet 46 and back sheet 48 are sealed along their marginal edge portions 50 to form a flexible bag container. Receptacle 12 is also provided with a drainage valve 52 mounted in the lower portion thereof which may be of identical construction to the drainage valve 44 installed on the meter. In the preferred embodiment sheets 46 and 48 are made of polyvinyl chloride plastic film. The front sheet 46 of receptacle 12 is provided with scale 54 for purposes of indicating the approximate amount of liquid therein.

Figure 2:
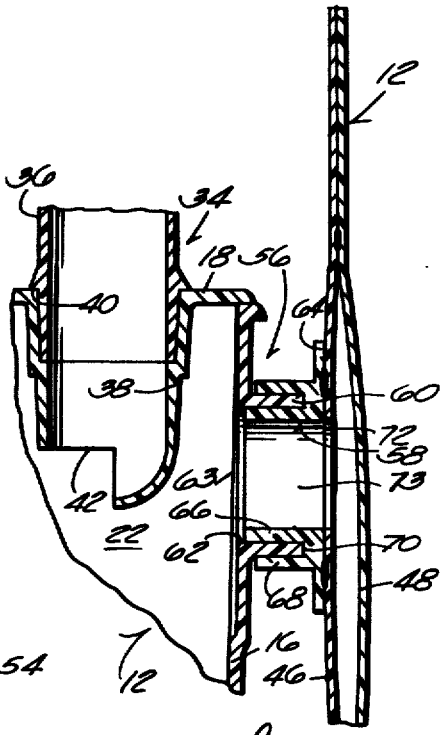
FIG. 2 is an enlarged fragmentary sectional view taken along line 2—2 of FIG. 1.

As best shown in FIG. 2, a liquid communication means 56 is provided between the upper portions of meter 10 and drainage receptacle 12. Communication means 56 is comprised of a tubular fitting 58 and a mating collar 60 surrounding an opening 62 in the rear wall 16 of meter 10 and formed integrally therewith. A slight depression 63 is formed on the inside surface of the rear wall 16 around the opening into collar 60 to facilitate flow of liquid through the opening. Fitting 58 has a flange portion 64 sealed to the front sheet 46 of receptacle 12 and a pair of concentrically spaced circular walls 66,68 providing a groove 70 therebetween in which collar 60 is sealed to complete the communication means between the two containers. An opening 72 in the front sheet 46 of receptacle 12 completes a liquid conduit 73 between the two containers having a relatively large diameter (approximately 0.6 inch) and a short longitudinal length (approximately 0.37 inch).

Figure 3:
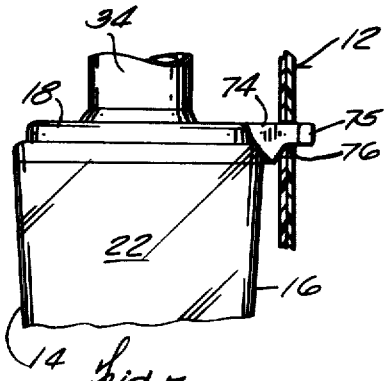
FIG. 3 is an enlarged fragmentary sectional view taken along line 3—3 of FIG. 1.

As best shown in FIG. 3, in addition to the liquid conduit connection 56 between the upper left hand portions of meter 10 and receptacle 12 (as viewed in FIG. 1), a strictly mechanical connection is provided between the upper right hand portions of the meter and receptacle. Such mechanical connection is in the form of a projecting arm 74 formed on the top wall 18 of the meter. Arm 74 has a transverse lip 75 formed at the end thereof adapted for engagement in an opening 76 formed in the receptacle. The sheets 46 and 48 of receptacle 12 are sealed to each other around opening 76 to prevent leakage of fluid from inside the receptacle. The combination of the fluid and mechanical connection 56 and the strictly mechanical connection arm 74 between the meter 10 and receptacle 12 serves to stabilize the mechanical connection between the containers.

In use the combination urine meter and drainage receptacle of the present invention is supported in a vertical hanging position adjacent the patient by a suitable cord support means 77 fastened to the top portion of receptacle 12. Urine draining into meter 10 through tube 32 and drip chamber assembly 34 will collect first in lower section 28, then in intermediate section 26 and then in upper section 24 of the meter. The amount of urine drained into the meter and its rate of flow can be measured by reference to scale 30. As drainage continues the level of liquid in the meter will eventually rise to the level of liquid communication means 56 after which liquid will flow through conduit 73 from meter 10 into drainage receptacle 12.

Figure 4:
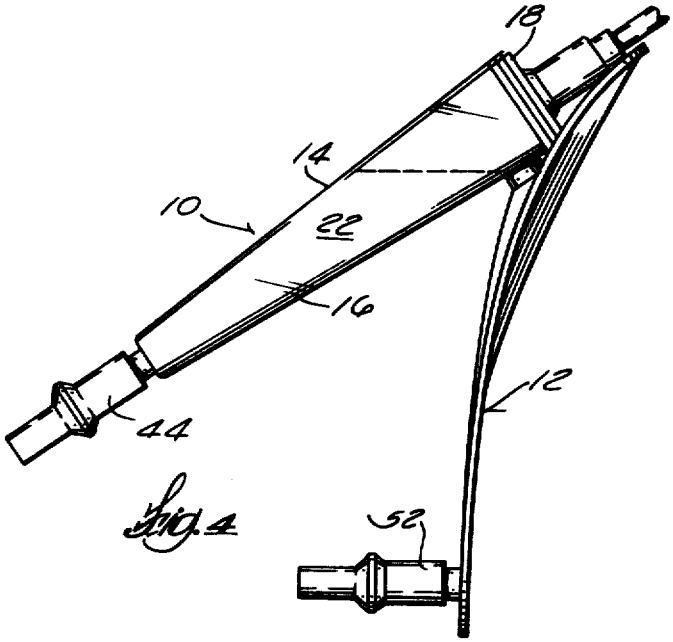
FIG. 4 is a side elevation view of the combination urine meter and drainage receptacle shown in FIG. 1 with the parts thereof shown in the meter drainage position.

It is often desirable (particularly when measuring flow rate) to drain urine from meter 10 into receptacle 12 at some point before meter 10 becomes completely filled. This can be simply and effectively accomplished by tilting meter 10 with respect to flexible receptacle 12 from its vertical hanging position (FIG. 1) to its drainage position shown in FIG. 4. When so tilted, liquid in meter 10 will readily flow from the meter into depression 63 and then through conduit 73 into receptacle 12. It will be noted that due to the relative movement between meter 10 and receptacle 12 provided by the particular construction of the combination, when meter 10 is tilted as shown in FIG. 4, receptacle 12 will remain in substantially vertical hanging position to thereby insure a positive drainage flow between the two containers.

The body of urine meter 10 can be manufactured from any variety of materials which are impervious to water. In addition to cellulose propionate as specified previously, examples of materials suitable for this purpose are polyvinyl chloride, cellulose acetate, cellulose butyrates and styrene. The meter 10 may be formed by any variety of methods well known in the art such as injection molding, blow molding, rotational molding or vacuum forming.

As indicated previously, drainage receptacle 12 may be comprised of a bag made by sealing together front and back sheets of flexible material along their outer edges. In addition to polyvinyl chloride as specified previously, examples of materials suitable for construction of the front and back sheets forming the receptacle include flexible films of polyethylene, polypropolene and the like.

Although the present invention is concerned mainly with the provision of a meter and drainage receptacle for urine, it should be understood that it could also be utilized in the measurement and storage of other liquids.

We claim:

1. A combination urine meter and drainage receptacle comprising:

a liquid meter of semi-rigid material having at least one volume calibrated chamber and an inlet opening through which liquid may be introduced into the interior thereof, said meter having an upper portion in which said inlet opening is located and a lower portion in which said liquid can accumulate;

a liquid draining receptacle in the form of a bag made of flexible material, said bag having an upper portion positioned adjacent said meter upper portion; and a liquid communication means for said meter and drainage receptacle comprising a liquid conduit extending from the upper portion of said meter to the upper portion of said drainage receptacle, said liquid communication means adapted to permit relative movement of said meter with respect to said drainage receptacle to thereby facilitate drainage of liquid from the interior of the meter through said liquid conduit and into said drainage receptacle by simply tilting said meter with respect to said drainage receptacle, said liquid communication means including a semi-rigid tubular assembly fastened at one end to said meter and fastened at its other end to said liquid drainage receptacle, said semi-rigid tubular assembly comprised of a tubular fitting having a flange sealed to one wall of said liquid drainage receptacle, said tubular fitting having a pair of concentrically spaced circular walls providing a groove therebetween, said tubular assembly further including a collar formed integrally with one wall of said meter, said collar being sealed in said groove by said tubular fitting to thereby provide a fluid tight liquid conduit between said meter and said receptacle.

2. A combination urine meter and drainage receptacle according to claim 1 in which there is a depression formed on the inside surface of said one wall of said liquid meter around said collar to facilitate flow of liquid through said collar.

3. A combination urine meter and drainage receptacle according to claim 2 in which said liquid receptacle is provided with a closable drainage valve mounted in the lower portion thereof which may be opened and closed to permit liquid to be drained out of the interior of said liquid receptacle.

4. A combination urine meter and drainage receptacle comprising:

a liquid meter of a semi-rigid material having at least one volume calibrated chamber and an inlet opening through which liquid may be introduced into the interior thereof, said meter having an upper portion in which said inlet opening is located and a lower portion in which said liquid can accumulate;

a liquid drainage receptacle in the form of a bag made of flexible material, said bag having an upper portion positioned adjacent said meter upper portion; and a liquid communication means for said meter and drainage receptacle extending from the upper portion of said meter to the upper portion of said drainage receptacle, said liquid communication means including a semi-rigid tubular assembly fastened at one end to said meter and fastened at its other end to said liquid drainage receptacle, said semi-rigid tubular assembly of said liquid communication means comprised of a tubular fitting having a flange sealed to one wall of said liquid drainage receptacle, said tubular fitting having a pair of concentrically spaced circular walls providing a groove therebetween, said tubular assembly further including a collar formed integrally with one wall of said meter, said collar being sealed in said groove of said tubular fitting to thereby provide a fluid tight liquid conduit between said meter and said receptacle.

5. A combination urine meter and drainage receptacle according to claim 4 in which there is a depression formed on the inside surface of said one wall of said liquid meter around said collar to facilitate flow of liquid through said collar.

6. A combination urine meter and drainage receptacle comprising:

a liquid meter having at least one volume calibrated chamber and an inlet opening through which liquid may be introduced into the interior thereof, said meter having an upper portion in which said inlet opening is located and a lower portion in which the liquid entering through said opening can accumulate;

a liquid drainage receptacle in the form of a bag made of flexible material, said bag having an upper portion positioned adjacent said meter upper portion; and a liquid communication means for said meter and drainage receptacle comprising a liquid conduit extending from the upper portion of said meter to the upper portion of said drainage receptacle, said liquid communication means adapted to permit relative movement of said meter with respect to said drainage receptacle to thereby facilitate drainage of liquid from the interior of the meter through said liquid conduit and into said drainage receptacle by simply tilting said meter with respect to said drainage receptacle, said liquid conduit of said liquid communication means comprised of a short, semi-rigid, horizontally extending tubular assembly fastened at one end to said liquid meter and fastened at its other end to said liquid drainage receptacle, *said tubular assembly having no part which moves relative to any other part of said assembly, said tilting of said meter with respect to said drainage receptacle being accomplished by the flexing of said drainage receptacle in the area at which it is fastened to said tubular assembly,* said tubular assembly serving to at least partially support said liquid meter on said liquid drainage receptacle in a side-by-side relationship with the meter and receptacle positioned at substantially the same elevation;

said combination further characterized by a hollow tube which opens into the interior of said liquid meter through a drip tube assembly mounted in the top wall of the meter, said drip tube assembly comprised of an upper tubular member and a lower tubular drip projection formed integrally with said top wall, said tubular member being telescopically engaged with said projection and sealed therein, said drip projection portion further having an opening in the bottom portion thereof through which liquid flowing through said tube enters the interior of said meter.

7. A combination urine meter and drainage receptacle according to claim 6 in which said drip projection is in the form of a tube having a rounded end with said end having a cut-out portion to provide said opening therein.

8. A combination urine meter and drainage receptacle comprising:

a liquid drainage receptacle in the form of a bag made of flexible material, said bag having a support means fastened to the upper portion thereof which is adapted to support said receptacle in a vertical hanging position when in operative use;

a liquid meter of a semi-rigid material having at least one volume calibrated chamber and an inlet opening through which liquid may be introduced into the interior thereof, said meter having an upper portion in which said inlet opening is located and a lower portion in which said liquid entering through said opening can accumulate, said meter positioned in substantially parallel, closely adjacent relationship with said receptacle with the upper portion of said receptacle positioned opposite the upper portion of said meter; and a liquid communication means for said meter and said drainage receptacle extending from the upper portion of said meter to the upper portion of said drainage receptacle, said liquid communication means including a short semi-rigid horizontally extending tubular assembly fastened at one end to said meter and fastened at its other end to said liquid drainage receptacle, said communication means operable to facilitate drainage of liquid from the interior of said meter through said tubular assembly and into said drainage receptacle by tilting said meter from its normal position parallel to said receptacle to its drainage position at an angle with respect to said receptacle, said tilting of said meter for drainage being accomplished without altering the vertical hanging position of said receptacle so that complete drainage of said meter can be accomplished without detachment of the meter from the receptacle, *said tubular assembly having no part which moves relative to any other part of said assembly, said tilting of said meter with respect to said drainage receptacle being accomplished by the flexing of said drainage receptacle in the area at whch it is fastened to said tubular assembly,* said tubular assembly further serving to at least partially support said liquid meter on said drainage receptacle in a side-by-side relationship with the meter and receptacle positioned at substantially the same elevation.

9. A combination urine meter and drainage receptacle according to claim 8 wherein said liquid meter includes a sampling valve mounted in the lower portion thereof which may be opened and closed to permit liquid to be drained out of the interior of said meter.

10. A combination urine meter and drainage receptacle according to claim 8 in which there is a hollow tube which opens into the interior of said liquid meter through a drip tube assembly mounted in the top wall of the meter, said drip tube assembly comprised of an upper tubular member and a lower tubular drip projection formed integrally with said top wall, said tubular member being telescopically engaged with said projection and sealed therein, said drip projection portion further having an opening in the bottom portion thereof through which liquid flowing through said tube enters the interior of said meter.

11. A combination urine meter and drainage receptacle according to claim 10 in which said drip projection is in the form of a tube having a rounded end with said end having a cut-out portion to provide said opening therein.

12. A combination urine meter and drainage receptacle according to claim 8 in which the longitudinal length of said semi-rigid tubular assembly is less than 0.5 inches and the diameter of said liquid conduit is at least 0.3 inches.

13. A combination urine meter and drainage receptacle according to claim 8 in which said liquid meter has an arm formed thereon in the upper portion thereof and spaced from said liquid communication means, said arm adapted for engagement with said liquid drainage receptacle.

14. A combination urine meter and drainage receptacle according to claim 8 wherein said semi-rigid material of said liquid meter is transparent in the area on which it is calibrated.

* * * * *

UNITED STATES PATENT AND TRADEMARK OFFICE

CERTIFICATE OF CORRECTION

PATENT NO. : Re. 30,607

DATED : May 12, 1981

INVENTOR(S) : James G. Manschot, Byron L. Mather, Larry A. Salvadori

It is certified that error appears in the above—identified patent and that said Letters Patent is hereby corrected as shown below:

Column 1, Line 16, After "Nos." delete "3,683,984 and substitute therefor ---3,683,894---

Column 6, Line 48, Claim 8, After "at" and before "it" delete "whch" and substitute therefor ---which---

Signed and Sealed this

*Twenty-eighth* Day of *July 1981*

[SEAL]

*Attest:*

GERALD J. MOSSINGHOFF

*Attesting Officer*

*Commissioner of Patents and Trademarks*